(12) United States Patent
Rault et al.

(10) Patent No.: US 11,077,303 B2
(45) Date of Patent: Aug. 3, 2021

(54) IMPLANTABLE PROBE FOR ELECTRICAL STIMULATION AND/OR FOR DETECTION OF ELECTRICAL POTENTIALS ON AN ORGAN

(71) Applicant: SORIN CRM SAS, Clamart (FR)

(72) Inventors: Maxime Rault, Paris (FR); Patrick Le Gousse, Viry Chatillon (FR)

(73) Assignee: Sorin CRM SAS, Clamart (FR)

( * ) Notice: Subject to any disclaimer, the term of this patent is extended or adjusted under 35 U.S.C. 154(b) by 226 days.

(21) Appl. No.: 16/062,074

(22) PCT Filed: Dec. 9, 2016

(86) PCT No.: PCT/EP2016/080390
§ 371 (c)(1),
(2) Date: Jun. 13, 2018

(87) PCT Pub. No.: WO2017/102578
PCT Pub. Date: Jun. 22, 2017

(65) Prior Publication Data
US 2018/0369588 A1   Dec. 27, 2018

(30) Foreign Application Priority Data
Dec. 14, 2015  (FR) ...................... 1562267

(51) Int. Cl.
*A61N 1/36*   (2006.01)
*A61N 1/05*   (2006.01)
*A61B 5/24*   (2021.01)
*A61B 5/00*   (2006.01)
*A61N 1/362*  (2006.01)

(52) U.S. Cl.
CPC ............ *A61N 1/36053* (2013.01); *A61B 5/24* (2021.01); *A61N 1/0551* (2013.01); *A61N 1/0556* (2013.01); *A61N 1/0563* (2013.01); *A61B 5/6877* (2013.01); *A61B 2562/125* (2013.01);
(Continued)

(58) Field of Classification Search
None
See application file for complete search history.

(56) References Cited

U.S. PATENT DOCUMENTS 4,602,624 A    7/1986  Naples et al.
7,640,065 B1  12/2009  Kroll
(Continued)

OTHER PUBLICATIONS

International Search Report and Written Opinion on International Patent Application No. PCT/EP2016/080390 dated Mar. 2, 2017. 11 pages.

*Primary Examiner* — Joseph M Dietrich
(74) *Attorney, Agent, or Firm* — Foley & Lardner LLP

(57) ABSTRACT

This disclosure relates to an implantable probe for electrical stimulation of an organ and/or for detection of electrical potentials on this organ. The probe comprises a distal end able to come into contact with the tissues of the organ, this end comprising an insulating substrate, and at least one conductive interface carried by the substrate. The probe further comprises a probe body having at least one bonding conductor connected to a respective conductive interface. The conductive interface comprises at least one deformable conductive wire, at least partially exposed, with a woven, embroidered, braided or knitted configuration for anchoring the deformable wire to the substrate.

8 Claims, 6 Drawing Sheets

(52) U.S. Cl.
CPC ......... *A61N 1/3627* (2013.01); *A61N 1/36114* (2013.01)

(56) References Cited

U.S. PATENT DOCUMENTS

| | | |
|---|---|---|
| 2002/0103511 A1 | 8/2002 | Alferness et al. |
| 2010/0262214 A1* | 10/2010 | Robinson ............. A61N 1/0551 607/116 |
| 2013/0226272 A1 | 8/2013 | Cattaneo et al. |
| 2014/0228922 A1 | 8/2014 | Gindele et al. |
| 2014/0288577 A1 | 9/2014 | Robinson et al. |
| 2015/0066122 A1 | 3/2015 | Govea |
| 2015/0076517 A1* | 3/2015 | Terai ................... H01L 29/1608 257/77 |

* cited by examiner

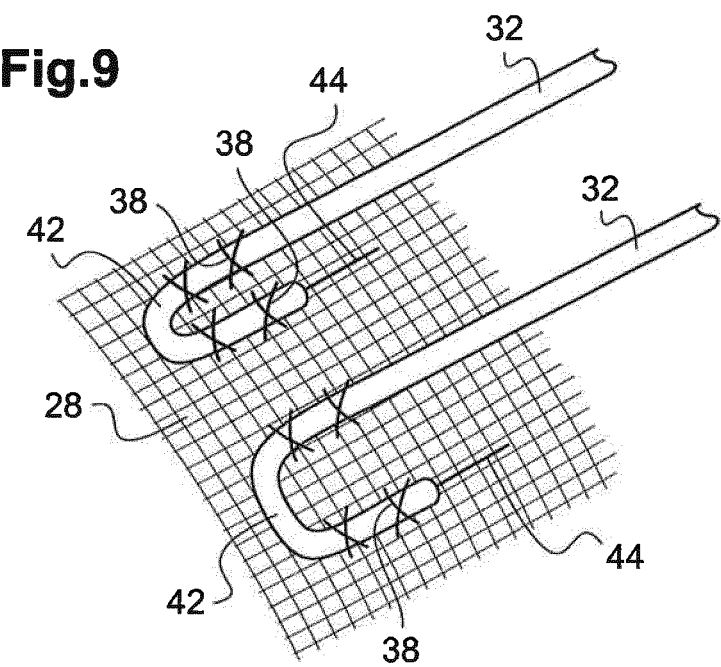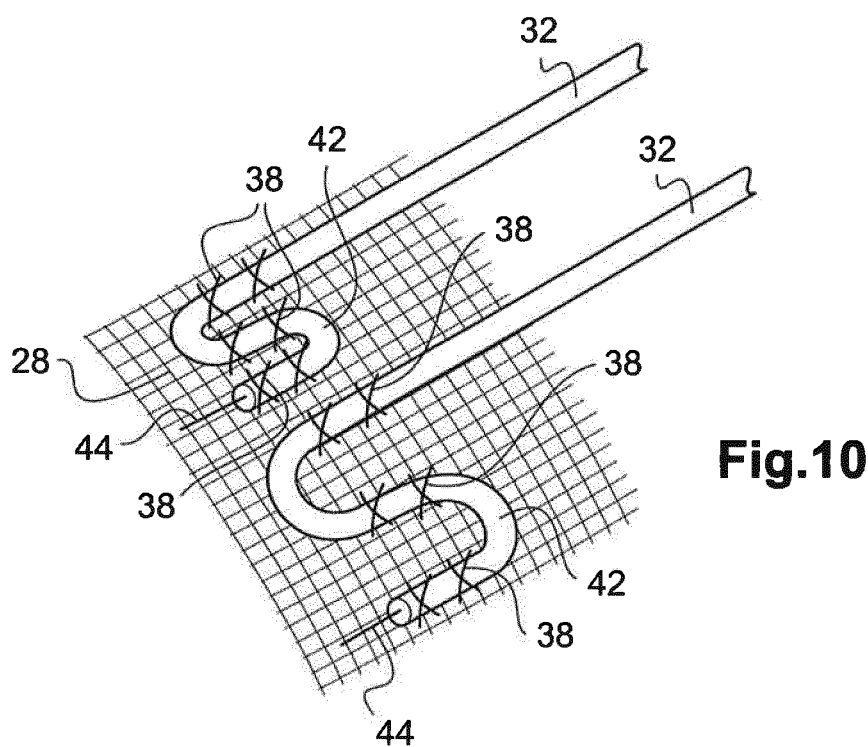

Fig.14
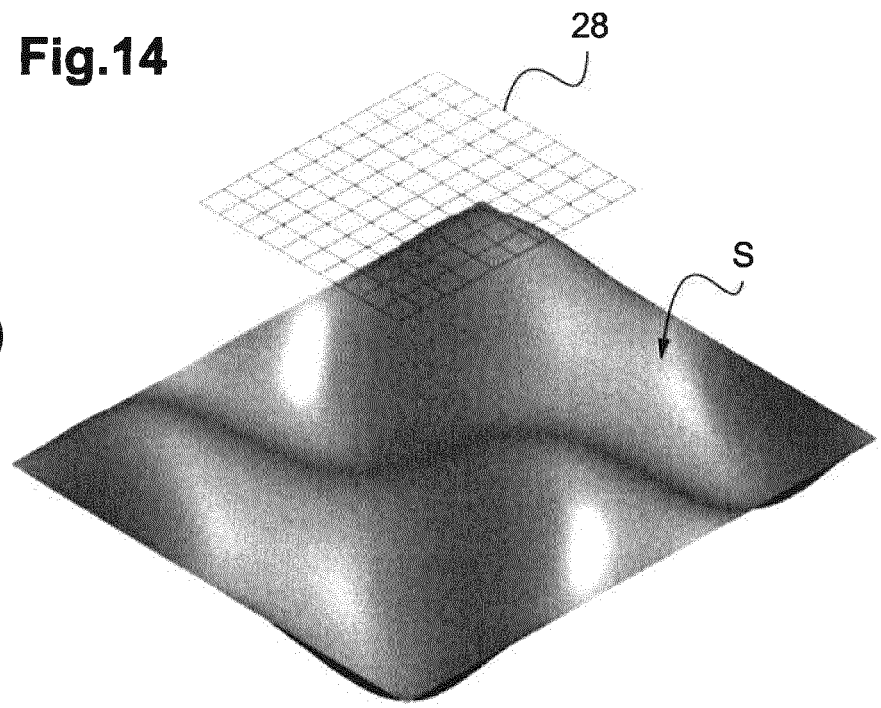
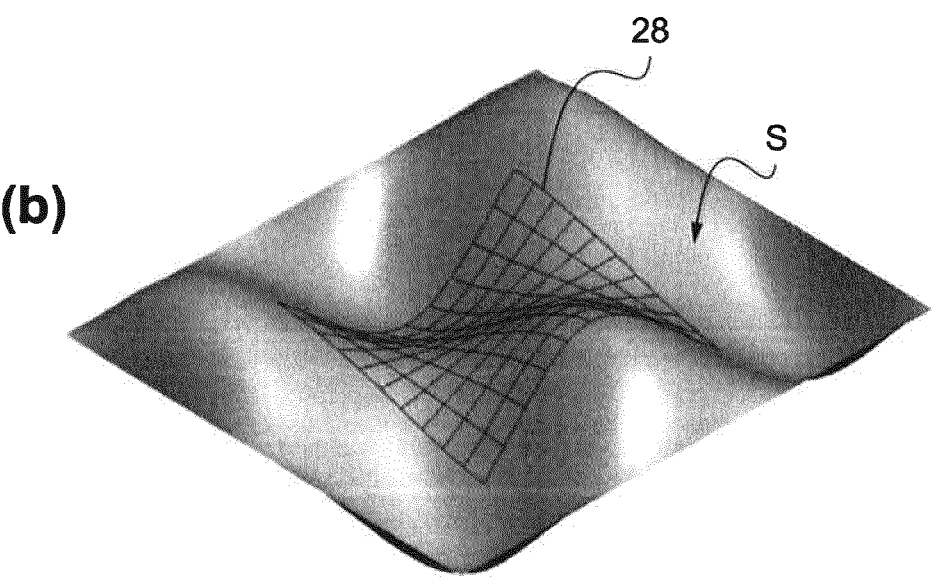

IMPLANTABLE PROBE FOR ELECTRICAL STIMULATION AND/OR FOR DETECTION OF ELECTRICAL POTENTIALS ON AN ORGAN

CROSS-REFERENCE TO RELATED PATENT APPLICATIONS

This application is a 371 U.S. National Application of International Application No. PCT/EP2016/080390, filed Dec. 9, 2016, which claims the benefit of and priority to French Patent Application No. 1562267, filed Dec. 14, 2015, which is incorporated herein by reference in its entirety.

BACKGROUND

The invention relates to "active implantable medical devices" as defined by Directive 90/385/EEC of 20 Jun. 1990 of the Council of the European Communities, and more specifically devices comprising one or more implantable electrodes applied against an organ to allow the electrical stimulation thereof and/or collection of electrical potentials from such an organ.

The invention will be more particularly described in the context of the stimulation of the nerves, especially the stimulation of the vagus nerve in the case of therapies referred to as VNS (Vagus Nerve Stimulation).

However, this application is only given by way of example and has no restrictive character, as the invention may be used to stimulate/detect any other organ, in fields such as neurostimulation, neurosurgery, cardiology, electrical stimulation of tissues, etc., whenever it is necessary to possess implanted electrodes comprising one or more interfaces with biological tissues of a target organ.

In the case of nerve stimulation, a predominantly flat electrode which has just been wound directly around the outer wall of the nerve to be stimulated is used. The electrode is provided with conducting interfaces connected to bonding conductors then extending along a probe body to an opposite proximal end, coupled to a generator delivering controlled electrical pulses.

In other applications, a tubular electrode is inserted into a vessel so as to locate the conductive interfaces as close as possible to the inner wall of the vessel, in order to electrically contact the electrodes of the device with nearby nerve fibers extending close to the vessel.

In still other applications, the target organ consists of muscle fibers, brain tissue, heart tissue (e.g, in an application to a defibrillation electrode, etc.).

The invention more particularly relates to the probe portion implanted against the target organ, hereinafter referred to as "end" or "distal end", which allows to maintain the electrodes in contact with the target organ or in close proximity thereof.

In the particular example of the vagus nerve's stimulation, according to the elongated, approximately cylindrical configuration of the nerve, the end is in the form of a tubular shaped sleeve, wrapped around the nerve. The sleeve is generally made of an elastomer such as silicone, due to the excellent biocompatibility of this material, and supports on its inner face, applied against the nerve, the stimulation/detection electrodes.

This sleeve is for example made as described in U.S. Pat. No. 4,602,624 A, from two sheets of elastomer laminated together, one of them having been previously stretched in a preferred prestressing direction. Thus, a self-winding and self-adaptable end to the nerve's diameter is made: regarding its positioning, all the surgeon has to do is to unwind the sleeve, place it under the nerve and then release it, so the sleeve come and wrap itself around the nerve. If one chooses an inner diameter at rest slightly smaller than the diameter of the nerve, this sleeve, with its electrodes, will always remain tightly located against the nerve, even if the diameter thereof varies (since the vagus nerve has an average diameter between 1.9 mm and 2.5 mm, depending on the patients).

Regarding more specifically the electrodes and the way they are carried out, a first technique, the most widespread, consists in bringing contacts and crimping them on the connective conductor that extends into the probe body and ensure the electric coupling with the pulse generator located at the proximal opposite end of the probe body. The mechanical strength of the assembly is high, but this technology makes it only possible to have a limited number of contacts (usually 4-6 contacts) at the vagus nerve's periphery, due to the feasible minimum size in practice, around a millimeter. In addition, in the case of the vagus nerve's stimulation, the wider the contacts are, the less it will be possible for the sleeve to be wound the closest to the nerve.

Another technique consists in carrying out the contacts from a metal sheet held on the surface of the self-winding silicone sleeve, thereby forming an annular contact with the nerve after positioning of the sleeve. One of the limitations of this technology holds in the fact that the electrode is annular and thus stimulate the entire periphery of the nerve, without any possibility of creating an array of discrete electrodes stimulating specific spots of the nerve's periphery. Another difficulty lies in the need to ensure that the metal sheet remains in place while in contact with the nerve, even in the event of the end's deformation.

A third technique, recently developed, consists in laying the contacts down by chemical or physical vapor deposition (PVD/CVD) on the surface of a biocompatible organic substrate, said substrate being then fixed to the silicone sleeve. One difficulty here lies in the linkage, after filing of these contacts with the bonding conductors, which is a very delicate procedure. In addition, the mechanical strength of this type of electrode is still very limited, the interface between the substrate and the contact being a sensitive area. And since it is necessary to enable a winding of the electrode, this winding leads to shears at the interfaces, which can quickly degrade the good adhesion between the contacts and the substrate.

In any event, none of the techniques proposed to date provide a high mechanical flexibility, which would allow a proper application of the end against the target organ.

Yet, it is highly desirable that this probe end (typically, the self-windable sleeve around the nerve and the electrodes carried by the sleeve) matches the target organ's surface. Indeed, this close contact is required to lower the electrical stimulation threshold and thus avoid applying excessively high currents that could induce undesirable side effects and, in any case, would shorten the implanted generator's lifespan.

Another important requirement to be met is that, from the mechanical standpoint, the probe's end only applies minimal constraints to the target organ, both at the time of implantation and after, and this despite the possible displacements of the organ, its possible swelling, etc. Some mechanical constraints applied broadly (sleeve too tight) or locally (at a protrusion of the probe's end in contact with the nerve) would indeed have a tendency to cause an inflammation of the target organ, obviously harmful.

These conditions are not easily met with existing probe ends, in particular:

- due to the inevitable rigidity of the self-winding sleeve (or similar interface), even if the said sleeve is made of a very flexible material: indeed, due to its elastic nature this sleeve necessarily exerts a mechanical constriction force on the nerve, force that furthermore isn't consistent and can generate locally some relatively significant constraints;
- due to the fact that conventional electrodes all involve the deformation of metal parts that add their own rigidity to the sleeve's rigidity; and
- due to the fact that the self-windable sleeve defines an inner contact surface which is inherently a developable surface, whereas the target organ's outer surface is a non-developable surface. Even if the nerve has an approximately cylindrical shape, it is only an approximation and tangibly it can come into contact with the sleeve only in an imperfect manner, with contact areas creating mechanical constraints on the nerve and non-contact areas ineffective in terms of electrical stimulation.

Another disadvantage of these known techniques is the difficulty, due to technological constraints of implementation, to perform complex electrode configurations, such as arrays of specific electrodes to stimulate the target organ in a plurality of sites, possibly selectable based on the results obtained after clinical tests.

SUMMARY

The basic idea of the present invention suggests, instead of using the brought or deposited contacts, to achieve the conductive interface intended to come into contact with the target organ in the form of one or more elongated conductors assembled by weaving, embroidering, weaving or knitting to a substrate used as such like an end, that is to say not brought on an additional support (for example on a self-windable silicone sleeve).

The conductive interface could then be applied as accurately as possible against the target organ, for example to wrap itself around a nerve, with a relative deformability allowing the absorption of the organ's irregularities or dimensional changes (swelling, etc.) of said organ.

In addition, this configuration provides a great diversity in the contact geometries it allows to achieve, by weaving one or more conductive wire in a well-defined way in order to maximize the desired effects and/or identify specific sites of stimulation on the end.

More specifically, the invention proposes to this end an implantable probe comprising, in a manner known per se: a distal end able to come into contact with the tissues of the organ, this end comprising an isolating substrate and at least one conductive interface carried by the substrate; and a probe body comprising at least one bonding conductor connected to a respective conductive interface.

According to the invention, the substrate is a non-elastically deformable substrate. In addition, the conductive interface is devoid of additional elastically deformable support incorporating the substrate or associate to the substrate, it comprises at least one deformable conductive wire, at least partially stripped, and also comprises a woven, embroidered, braided or knitted configuration for anchoring the deformable wire to the substrate.

According to various advantageous subsidiary characteristics:

- the substrate is a sheet of homogenous material, or a woven or knitted weft, the interface can then be incorporated into the weave of the fabric or knitting's weft;
- the conductive wire of the conductive interface is formed by an extension of the connective conductor;
- the conductive wire of the conductive interface is separate from its respective bonding conductor, the conductive wire being electrically coupled to the bonding conductor, and the distal end of the bonding conductor is mechanically secured to the substrate.

BRIEF DESCRIPTION OF THE DRAWINGS

An embodiment of the present invention is described below with reference to the accompanying drawings, in which like references designate identical or functionally similar elements from one figure to another, and in which:

FIG. 9 illustrates a fourth example of the bonding conductor's mechanical fixing to the substrate.

FIG. 10 illustrates a fifth example of the bonding conductor's mechanical fixing to the substrate.

FIG. 14 illustrates the substrate before and after its application onto a complex surface.

DETAILED DESCRIPTION

Various embodiments of the device of the invention are described below.

Figure 1:
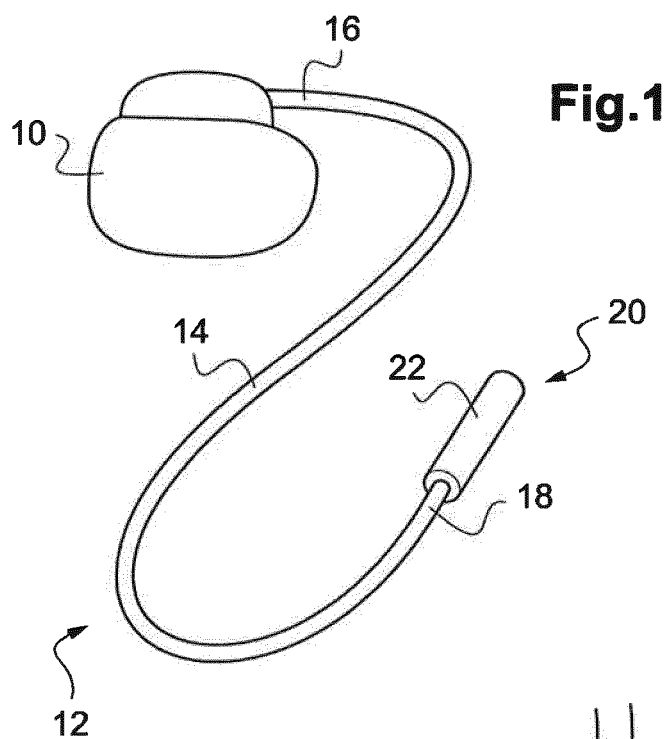
FIG. 1 illustrates all the elements of VNS stimulation device.

FIG. 1 illustrates all the elements of a VNS stimulation device.

This assembly comprises a generator of electrical pulses 10 connected to one (or more) probe(s) 12 for the delivery of the stimulation pulses produced by the generator and/or the collection of electrical potentials that will be analysed by the generator.

The probe 12 comprises an elongated tubular probe body 14, flexible, connected at its proximal portion 16 to the generator 10, typically via a plug connector, and comprising at its distal portion 18 a part, hereinafter referred to as "end" 20 able to come into contact with the tissues of an organ to be stimulated.

The probe body 14 includes a number of independent electrical conductors, hereinafter "bonding conductors" allowing to connect various electrodes of the end 20 to the homologous terminals of the generator 10. These bonding conductors are generally wound inside of the probe body in the form of a helical configuration so as to preserve the probe's flexibility while maintaining sufficient mechanical strength properties to avoid any breakage of a bonding conductor.

The end 20 may take many forms, and a configuration in which the termination is windable around a nerve, typically the vagus nerve, will be described more specifically hereinafter.

Figure 2:
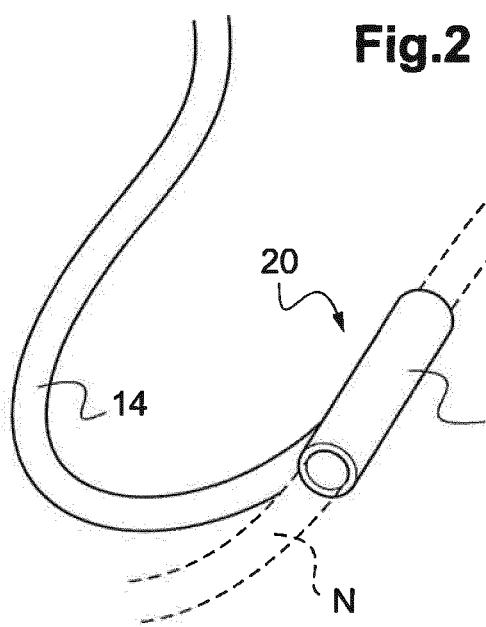
FIG. 2 illustrates more specifically an example of end windable around a nerve of the FIG. 1's device.

FIG. 2 illustrates an example of conventional end, made by means of a sleeve 22 self-windable around the nerve N so as to best match the shape thereof.

Figure 3:
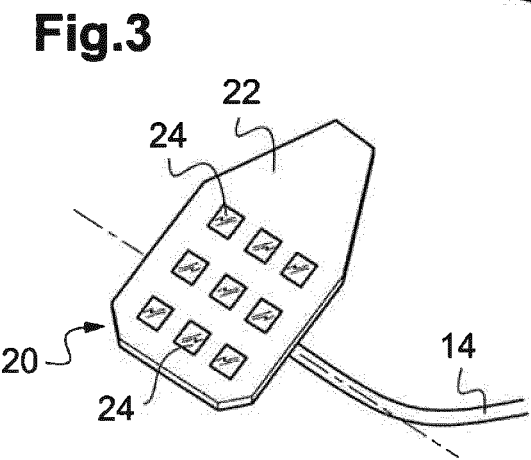
FIG. 3 illustrates, in its unwound form before positioning, a self-windable sleeve according to the state of the art forming the end of FIG. 2.

FIG. 3 illustrates, in an unwound form before positioning, the end's sleeve of FIG. 2.

This sleeve 22 is typically made from a sheet of elastically deformable material, for example silicone, carrying a plurality of electrically conductive pads (hereinafter "conductive interfaces") intended to be applied against a distinct stimulation site of the organ to stimulate. Each of the conductive interfaces 24 is connected to a respective conductor extending within the probe body 14 in order to be connected to a corresponding terminal of the generator, on its proximal side. The deformable sheet intended to form the sleeve 22 is advantageously prestressed so as to allow its self-winding from an initial position where the sheet is kept under stress in the expanded state (configuration of FIG. 3) to a final position where the sheet is freely wound helically, forming a sleeve around the organ (configuration of FIG. 2), the face carrying conductive interfaces 24 then bearing against the outer surface of the nerve N. Such a configuration of a self-windable sleeve is for example disclosed in the above-mentioned U.S. Pat. No. 4,602,624 A.

Figure 4:
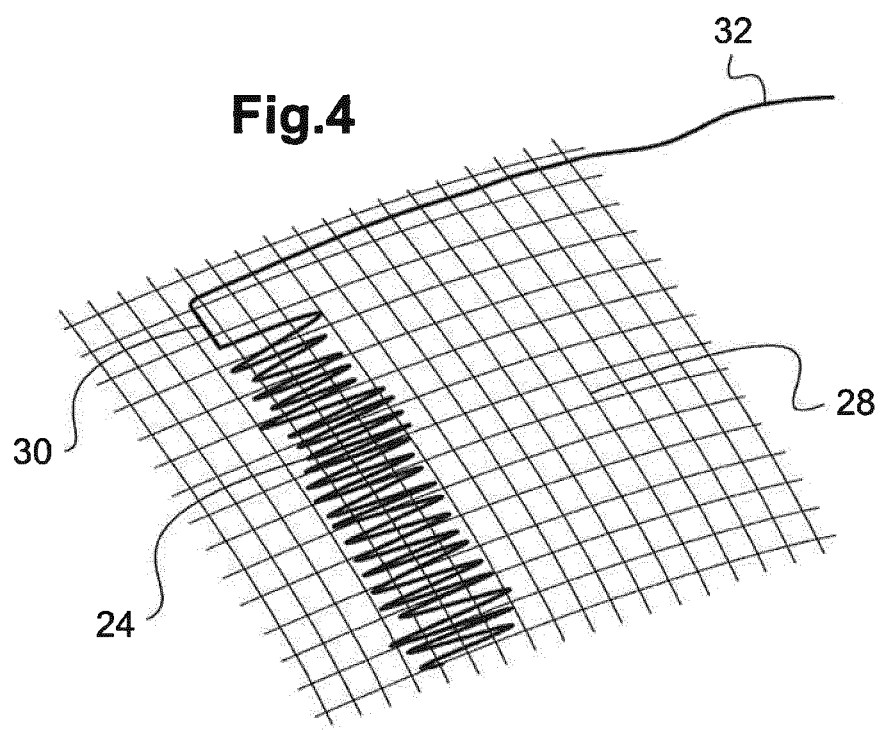
FIG. 4 illustrates an embodiment of an end implementing the teachings of the invention.

FIG. 4 illustrates a first embodiment implementing the teachings of the invention.

According to the invention, each of the conductive interfaces 24 is made from a deformable conductive wire 30, at least partially stripped and that, in the illustrated example, is anchored to a substrate 28 either by embroidering or another similar technique (weaving, braiding, knitting, etc.). This conductive wire 30 is connected to a respective bonding conductor 32. All of the end's bonding conductors 32 then extend inside the body probe to the remote generator located on the proximal side.

In the illustrated example of an end (FIG. 4), the conductive wire 30 is made by a direct extension of the bonding conductor and is embroidered on the substrate 28. The wire remaining after embroidering is retained and constitutes the bonding conductor 32, so that there is no discontinuity between these two elements.

Figure 5:
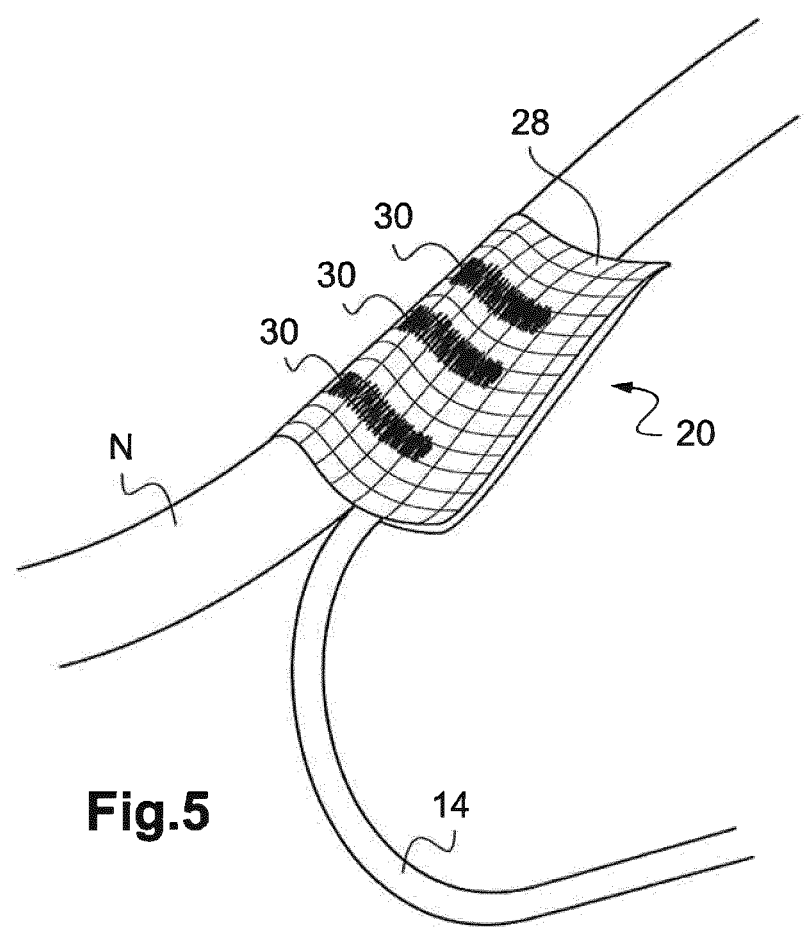
FIG. 5 illustrates the end of FIG. 4 applied against the target organ.

FIG. 5 illustrates the end of FIG. 4, applied against the target organ. As can be seen, the insulating woven substrate 28, which is very flexible and deformable, may be used in the manner of a gauze applied and wound around the nerve N. The regions where the conductive wires 30 were embroidered form peripheral stimulation electrodes of the nerve, and the protruding portion of the substrate 28 (portion which extends approximately onto an axial plane) connects the probe body 14 which is not directly in contact with the nerve N, decreasing strongly the transmission to the nerve N of constraints likely to be received by the probe body 14.

Generally, the substrate 28 can take various forms, depending on the specifics of the organ to stimulate.

Depending on the case, the substrate 28 may be made of: an isotropic homogeneous material; an anisotropic homogeneous material; an overall isotropic short fiber material; an overall anisotropic short fiber material; a unidirectional woven material; a bidirectional woven material; a multi-directional woven material; or any combination thereof.

Regarding the substrate's very own material, it can be: an active material such as nitinol; a biocompatible polymer material such as dacron, silicone, parylene, polyethylene, polyurethane or polyamide; a conductive material such as MP35N, platinum, a platinum-iridium alloy, a stainless steel such as 304 or 316; a resorbable material; a soluble material such as glucose; or any combination thereof.

The substrate can be reversibly deformable or not, with or without energy input from a mechanical, thermal, chemical, or other power source, internal or external to the substrate.

In the case of a woven substrate, the weft and warp wires that constitute it may or may not move relative to each other. Still in the case of a woven substrate, the wires can be woven at a right angle or at another angle (60°, 45°, 30°, 15° or any other angle). Furthermore, the weaving's pattern can be of any known type such as, twill, satin, taffeta or any other weaving.

Still in the case of a woven substrate, it is possible to use a fabric that is made of conductive wire or not, isolated or not. If conductive wires incorporated to the substrate are used, those can be stripped over their entire length, or else only partially stripped. In the latter case, stripping can be achieved mechanically, by laser ablation, chemical ablation, abrasion or any other method that expose to the external environment at least a portion of the wire's conductive material. It should be noted that it isn't required for the weft and warp wires to be conductive, but that this characteristic can be only reserved to only some of the weft and/or warp wires, the others being conventional non-conductive wires, constituting the substrate.

Finally, still in the case of a woven substrate, the conductive wires forming the conductive interface can be embedded to the weft forming the substrate at the time of weaving or knitting thereof, or added to the substrate during a subsequent step, for example by embroidering, the conductive wire passing through the substrate and being mechanically anchored to the latter.

The conductive interface designed to come into contact with the organ's tissues that need to be stimulated is then sewn, woven or embroidered on the substrate. The placement and the extent of the conductive interface may then be wisely selected and oriented so that the substrate remains flexible and/or expandable, the end thus being generally flexible and/or expandable, this characteristic being necessary to best match the organ that require stimulation and adapt itself to any potential deformation thereof.

The conductive interface may comprise a substrate with a weaving, braiding, embroidery direction or any other similar method properly selected, fitted with either woven, embroidered, sewn, electrodes or assembled by any similar method capable of fitting complex non-developable shapes.

In FIG. 14, the substrate 28 is illustrated in (a) before its application on the receiving surface S, and in (b) after application: it can be noted that the substrate 28 perfectly fit the complex shape S by allowing its components (weft and warp wires, etc.) to reposition themselves relatively to each other. Thus, there is no constant effort induced on biological tissues, while maintaining optimal contact.

The conductive wire constituting the conductive interface may be an isolated wire or not, single-stranded or stranded. If isolated, the conductive core will be exposed to the external environment by laser ablation, chemical ablation, manual cutting or any other mean allowing to expose the conductor.

Within the embodiment illustrated in FIG. 4, the conductive wire forming the end's conductive interface was an extension of the bonding wire, the latter then being mechanically bound to the substrate by appropriate means (stitching marks, glue dots, etc.).

In other embodiments, illustrated in FIGS. 6 to 13 and described hereafter, the conductive wire is separate from the bonding wire, and these two elements are electrically connected at a coupling point. This in particular allows for the use of a very thin wire regarding the conductive wire that constitutes the conductive interface; the bonding wire being thicker.

Regarding the bonding conductor, if it is in the form of an overall slender type, it may be, at least partially, mechanically bonded to the substrate by stitching, weaving, embroidering it directly or via a third-party material. The points thus formed can be continuous, regularly spaced or irregularly spaced.

The bonding conductor, or a portion thereof, can be mechanically bonded to the substrate by an adhesive, a weld, a braze, a local melting or any other method implementing the adhesive or cohesive characteristics of a third party or autogenous material.

In the case of an overall slender type bonding conductor and with a planar substrate, it is possible to secure the bonding conductor to the substrate by crossing one or multiple times the plane formed by the substrate, that is to say in the manner of one stitching mark passing alternately over and under the substrate.

Still in the case of an overall slender type conductor and with a planar substrate, a method to mechanically bind it, entirely or partially, with the substrate would be to perform generally one or more bends in the substrate's plane, with bending radii more or less important.

If the bonding conductor is in the form of an overall slender type, this conductor or a part of said conductor can be mechanically linked to the conductive wire constituting the conductive interface by welding, brazing, collage, wedging, embroidering, weaving, braiding, sewing, crimping, bonding or any other assembly method.

If the bonding conductor has a helical shape and if the substrate is planar, a method to bind it mechanically, or to bind a part of it, may cause one or more turns of one or more strands of the helix to be deformed so that these strands become parallel to the substrate plane, to which they could then be mechanically linked over all or part of their length by welding, brazing, collage, wedging, embroidering, weaving, braiding, sewing, crimping, bonding or any other process.

The conductors, whether used to make the bonding conductors or else the electrode conductors can be of various kinds. They can either be naturally biocompatible or coated with biocompatible materials such as 35NLT, MP35N, 304 stainless steel, 316L stainless steel, platinum, platinum-iridium alloy, other biocompatible metal, or any other biocompatible conductive or semi-conductive material. These conductors can be insulated or not. If that is the case, the insulating material can be, for example, ethylene and tetrafluoroethylene (ETFE).

Figure 6:
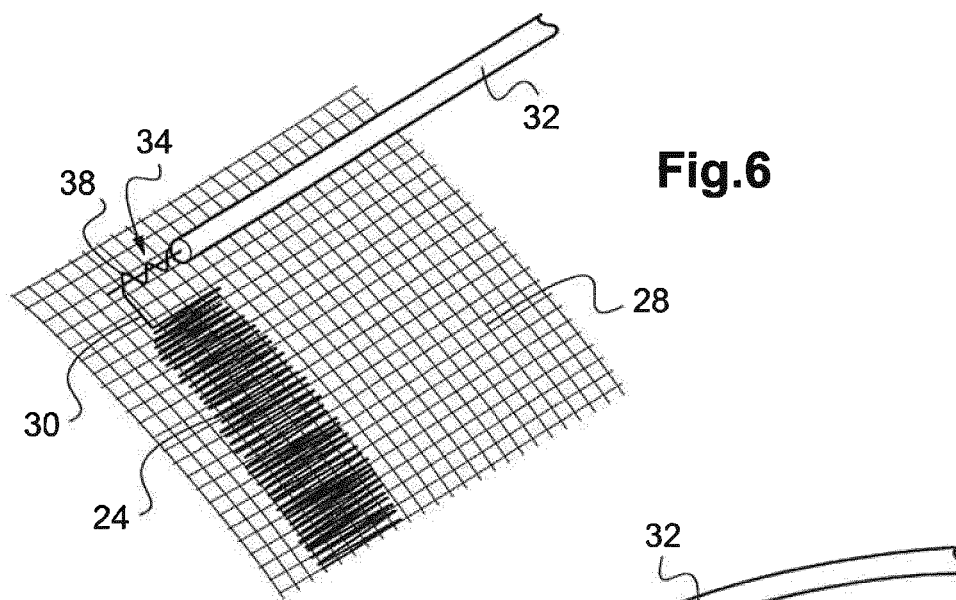
FIG. 6 illustrates a first example of mechanical fixing of the bonding conductor to the substrate.

FIG. 6 illustrates a first example of mechanical fixing of the bonding conductor to the substrate, at a coupling point 34.

In this example, the bonding conductor 32 which is electrically connected to the conductive wire 30 embroidered on the substrate 28, is anchored mechanically to the latter by stitching marks 38.

Figure 7:
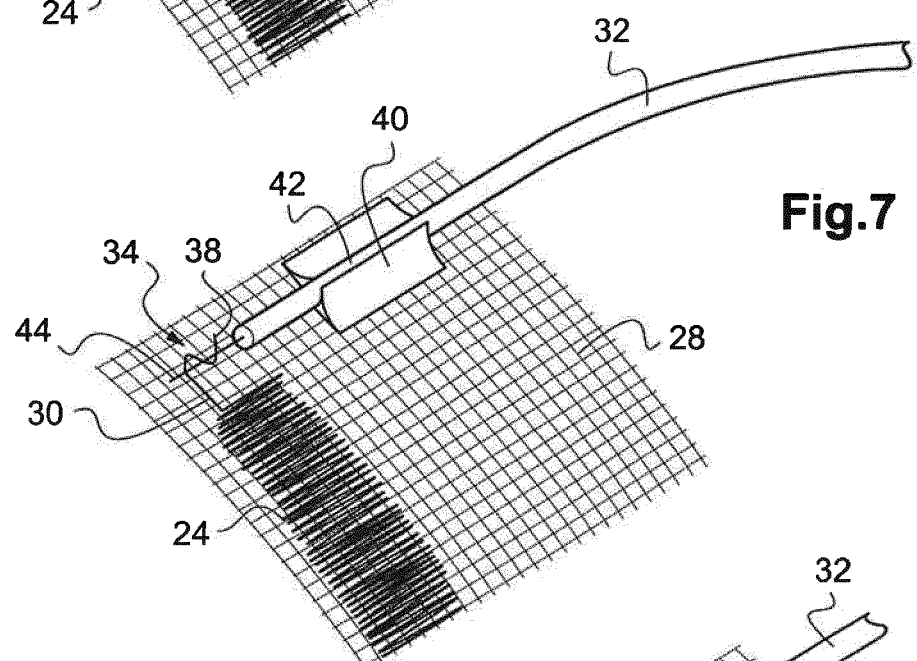
FIG. 7 illustrates a second example of the bonding conductor's mechanical fixing to the substrate.

FIG. 7 illustrates a second example of the mechanical fixing of the bonding conductor to the substrate.

In this example, the bonding conductor 32 is anchored to the substrate 28 via a glue dot 40 that surround the insulator 42 of the bonding conductor 32 (or the stripped portion) in an area close to the coupling point with the conductive wire 30, the bonding conductor's conductive core 44 being, as shown in the example of FIG. 6, mechanically anchored to the substrate 28 by stitching marks 38, so as to ensure recovery of potential constraints suffered in the area of the coupling with the conductive wire 30.

Figure 8:
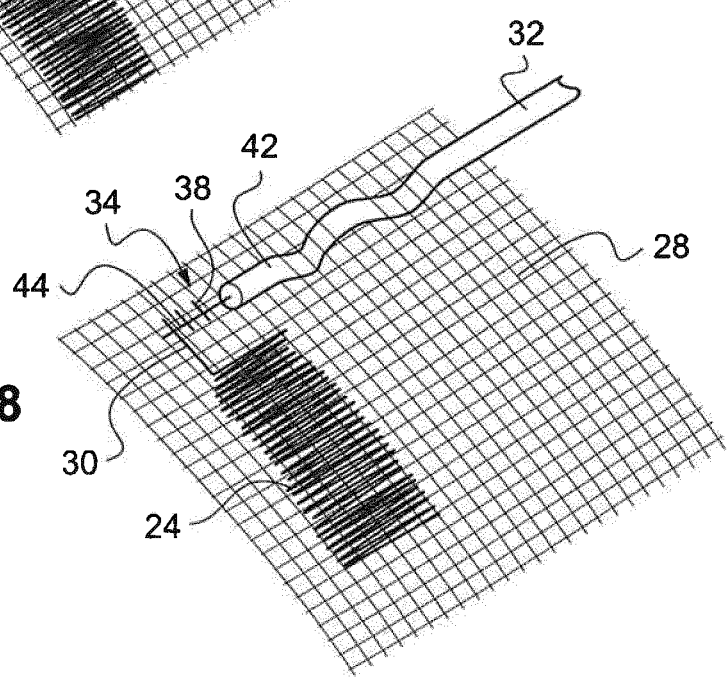
FIG. 8 illustrates a third example of the bonding conductor's mechanical fixing to the substrate.

FIG. 8 illustrates a third example of the mechanical fixing of the bonding conductor to the substrate.

In this example, the bonding conductor 32 is secured to the substrate 28 by weaving therewith, passing alternately below and above the substrate's plan. The anchoring of the bonding conductor 32 to the substrate is thus ensured in a purely mechanical manner, so without any use of a third-party material as in the case of collage 40 of FIG. 7. For the rest, the embodiment is identical to that of FIG. 7, the stitching marks 38 needed for the anchoring of the conductive core 44 to the substrate 28 being located in the vicinity of the link with the conductive wire 30.

FIG. 9 illustrates a fourth example of the mechanical fixing of the bonding conductor to the substrate.

In this example, the bonding conductor 32 ends in a U shape at its distal end's portion, just prior to the emergence area of the conductive core 44. The insulating sheath 42 (or the stripped portion) of the bonding conductor 42 is then secured to the substrate 28 by means of stitching marks made on each one of the U branches.

FIG. 10 illustrates a fifth example of the mechanical fixing of the bonding conductor to the substrate.

In this example, the end portion of the bonding conductor 32 is configured in a S shape at its distal end's portion, just prior to the emergence area of the conductive core 44. The insulating sheath 42 (or the stripped portion) of the bonding conductor 32 is then secured to the substrate 28 by means of stitching marks 38 made on each one of the S branches.

Figure 11:
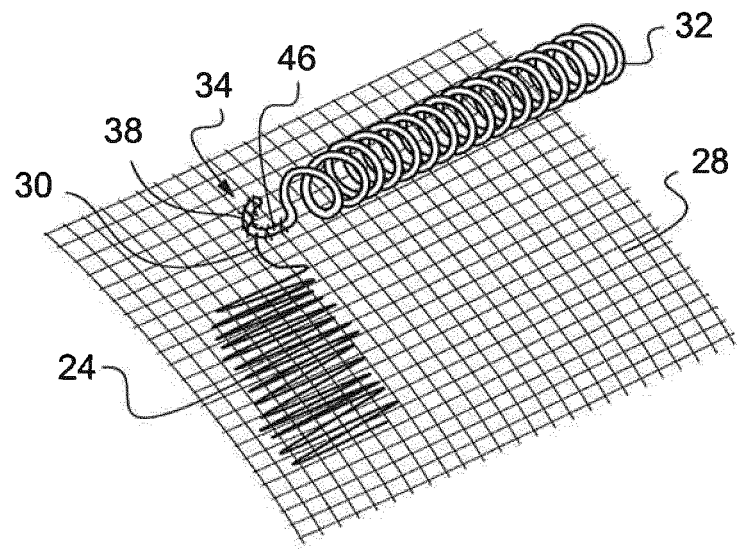
FIG. 11 illustrates an example of an embodiment wherein the bonding conductor has a helical shape.

FIG. 11 illustrates an example in which the bonding conductor 32 has a helical shape, typically corresponding to the case of a helical bonding conductor emerging from the interior of the probe body and which is not straightened in its end part. The bonding conductor's open end is then for example shaped as a loop or hook 46, which is secured to the substrate 28 by stitching marks 38, in the area close to the coupling with the conductive wire 30 that will form the probe end's conductive interface.

Figure 12:
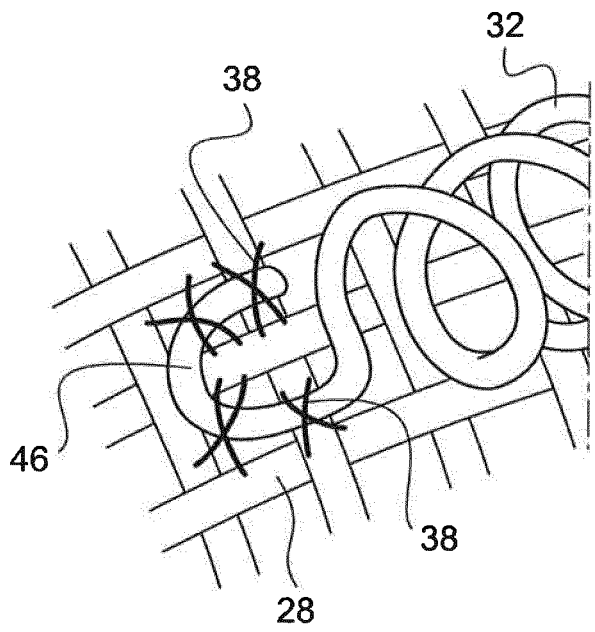
FIG. 12 is a detailed view, greatly enlarged, of the bonding conductor's end of FIG. 11.
Figure 13:
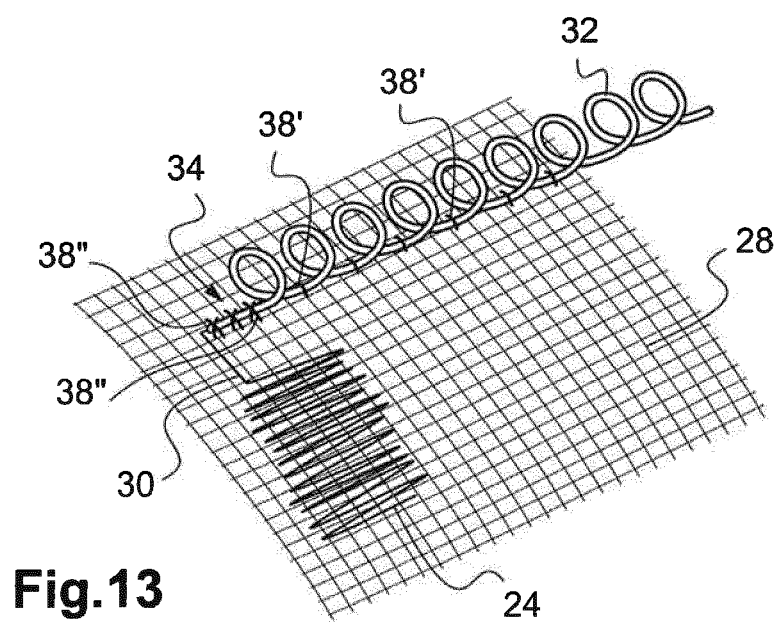
FIG. 13 illustrates another example of fixing of a helical bonding conductor to the substrate.

FIG. 12 is a detailed view, greatly enlarged, of the bonding conductor's end of FIG. 11, showing the hook 46 and the stitching marks 38 for attachment to the substrate 28.

FIG. 14 still illustrates another fixing method of a helical bonding conductor to the substrate.

In this example, the last turns of the bonding conductor 32 are anchored to the substrate by stitching marks 38' in the area where these turns come into contact therewith, the end portion of the bonding conductor 32 itself being anchored to the same substrate by other stitching marks 38" adjacent to the coupling area with the conductive wire 30 intended for forming the end's conductive interface.

The invention claimed is:
1. An implantable probe for electrical stimulation of an organ and/or for detection of electrical potentials on this organ, the implantable probe comprising:
 a distal end able to come into contact with the tissues of the organ, the distal end comprising:

an isolating substrate, wherein the isolating substrate is a non-elastically deformable substrate, and at least one conductive interface carried by the substrate; and a probe body comprising at least one bonding wire connected to one or more of the at least one conductive interface, wherein:

the at least one conductive interface is devoid of an additional elastically deformable support incorporating the isolating substrate;

the at least one conductive interface comprises at least one deformable conductive wire, at least partially stripped; and the at least one conductive interface comprises a woven, embroidered, braided or knitted configuration for anchoring the at least one deformable wire to the isolating substrate;

wherein the at least one deformable conductive wire of the at least one conductive interface is separate from its respective bonding wire, the at least one deformable conductive wire being electrically coupled to the bonding wire, and the distal end of the bonding wire being mechanically secured to the substrate by stitching the distal end of the bonding wire to the substrate.

2. The probe of claim 1, wherein the isolating substrate is a sheet of homogenous material.

3. The probe of claim 1, wherein the isolating substrate is a weft, either woven or knitted.

4. The probe of claim 3, wherein the at least one conductive interface is embedded to the weave of the fabric or knitting's weft.

5. An implantable probe for electrical stimulation of an organ and/or for detection of electrical potentials on this organ, the implantable probe comprising:

a distal end able to come into contact with the tissues of the organ, the distal end comprising:

a non-elastically deformable isolating substrate; and at least one conductive interface carried by the non-elastically deformable isolating substrate; and a probe body comprising at least one bonding wire connected to one or more of the at least one conductive interface, wherein:

the at least one conductive interface is devoid of an additional elastically deformable support incorporating the non-elastically deformable isolating substrate;

the at least one conductive interface comprises at least one deformable conductive wire, at least partially stripped, wherein the at least one bonding wire is thicker than the at least one deformable wire; and the at least one conductive interface comprises a woven, embroidered, braided or knitted configuration for anchoring the at least one deformable wire to the non-elastically deformable isolating substrate;

wherein the at least one deformable conductive wire of the at least one conductive interface is separate from its respective bonding wire, the at least one deformable conductive wire being electrically coupled to the respective bonding wire, and the distal end of the respective bonding wire being mechanically secured to the at least one deformable substrate.

6. The probe of claim 5, wherein the non-elastically deformable isolating substrate is a sheet of homogenous material.

7. The probe of claim 5, wherein the non-elastically deformable isolating substrate is a weft, either woven or knitted.

8. The probe of claim 7, wherein the at least one conductive interface is embedded to the weave of the fabric or knitting's weft.

* * * * *